(12) United States Patent
Taylor et al.

(10) Patent No.: US 6,267,849 B1
(45) Date of Patent: Jul. 31, 2001

(54) METHOD FOR THE PHOTOCATALYTIC CONVERSION OF GAS HYDRATES

(75) Inventors: Charles E. Taylor; Richard P. Noceti, both of Pittsburg; Bradley C. Bockrath, Bethel Park, all of PA (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 0 days.

(21) Appl. No.: 09/616,689

(22) Filed: Jul. 14, 2000

(51) Int. Cl.[7] .................... C07C 29/00; C07C 37/00
(52) U.S. Cl. .............................................. 204/157.9
(58) Field of Search ........................................ 204/157.9

(56) References Cited

U.S. PATENT DOCUMENTS 5,720,858 * 2/1998 Noceti et al. .................. 204/157.6

* cited by examiner

*Primary Examiner*—Edna Wong
(74) *Attorney, Agent, or Firm*—Mark P. Dvorscak; Robert J. Fisher; Virginia B. Caress

(57) ABSTRACT

A method for converting methane hydrates to methanol, as well as hydrogen, through exposure to light. The process includes conversion of methane hydrates by light where a radical initiator has been added, and may be modified to include the conversion of methane hydrates with light where a photocatalyst doped by a suitable metal and an electron transfer agent to produce methanol and hydrogen. The present invention operates at temperatures below 0° C., and allows for the direct conversion of methane contained within the hydrate in situ.

6 Claims, 5 Drawing Sheets

FIG. 4  MS ANALYSIS OF THE PHOTOCONVERSION OF GAS HYDRATE WITH ADDITION OF RADICAL INITIATOR

METHOD FOR THE PHOTOCATALYTIC CONVERSION OF GAS HYDRATES

The United States Government has rights to this invention pursuant to the employee/employer relationship of the inventors to the U.S. Department of Energy at the National Energy Technology Laboratory.

BACKGROUND OF THE INVENTION

1. Field of the Invention

The present invention relates to a method for converting methane hydrates to methanol and hydrogen through exposure to light. More specifically, the invention relates to converting methane stored in natural gas hydrates to methanol by the reaction of light.

2. Background of the Invention

Methane hydrates represent a large natural reserve of methane, and have an energy potential equal to more than twice that of all other fossil fuels combined. They are environmentally advantageous in that methane from hydrates produces less carbon dioxide than other forms of fossil fuels. Wide production could reduce carbon dioxide emissions by as much as twenty percent worldwide.

Methane hydrates are found in deep ocean sediments and Arctic permafrost as pressurized and frozen, icelike deposits: a frozen mixture of methane contained within an icewater mix. The reserves contain methane in a highly concentrated form, but the methane is difficult to extract and obtain. The U.S. Geological Survey has estimated the value of gas hydrates in the United States at 320,000 trillion cubic feet of gas, about 200 times the amount of conventional natural gas resources and reserves in the country.

The commercial extraction of methane hydrate is technologically difficult. To produce the methane contained in these hydrates, the hydrate must be thawed or the over pressure must be released. Either of these steps will release the methane from its natural deposit. However, how to collect and distribute the methane becomes problematic. Since the majority of the known hydrate deposits are not located near the natural gas transportation infrastructure, the methane must be compressed and shipped under pressure, or new pipelines need to be constructed.

In addition, current exploration techniques use to locate hydrate zones, such as sonar, are relatively crude, involving interpretative guess work.

Conversion of the methane while it is still contained in the hydrate avoids these problems.

U.S. Pat. No. 5,720,858, owned by the applicant herein, describes a method for converting methane and water into methanol and hydrogen using visible light and a catalyst. The conversion of methane disclosed by the '858 patent requires heating of methane saturated water to temperatures greater than 70° C.

There is thus a need for a method for producing methanol from methane hydrates, particularly a process that allows for the direct conversion of methane contained within the hydrate in situ.

SUMMARY OF THE INVENTION

The present invention discloses a method for converting methane hydrates to methanol, as well as hydrogen, through exposure to light. The process includes conversion of methane hydrates by light where a radical initiator has been added, and may be modified to include the conversion of methane hydrates with light where a photocatalyst (such as oxide salts of tungsten, titanium, or zirconium) doped by a suitable metal (such as copper, lanthanum, platinum, or lithium) and an electron transfer agent to produce methanol and hydrogen. The present invention operates at temperatures below 0° C., and allows for the direct conversion of methane contained within the hydrate in situ. The hydrate does not need to be harvested or the methane contained within the hydrate released for the conversion to occur.

BRIEF DESCRIPTION OF THE DRAWINGS

The above-mentioned and other features of the invention will become more apparent and be best understood, together with the description, by reference to the accompanying drawings, in which.

DETAILED DESCRIPTION OF THE INVENTION

Figure 1:
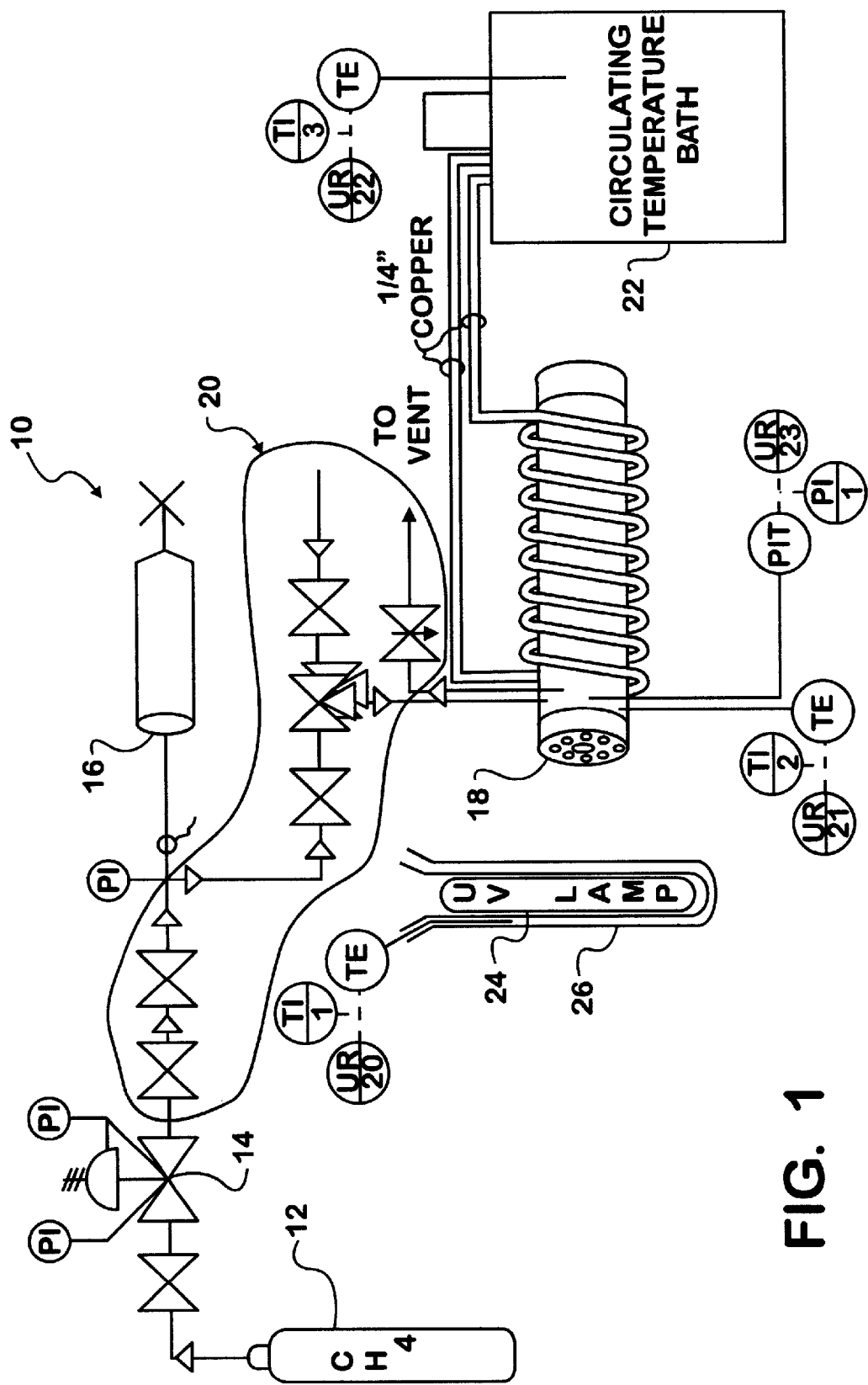
FIG. 1 is a schematic diagram of the invented method.

The present invention discloses a novel method for converting methane hydrates to methanol, as well as hydrogen, through exposure to light. Generally, a scheme for this conversion is represented as numeral 10 by the apparatus depicted by FIG. 1. A cylinder 12 contains ultra-high purity methane. The methane from cylinder 12 is passed through a pressure regulator 14, where the pressure is adjustable from atmospheric to a maximum of 2000 psig. If the cylinder pressure is lower than that required for the intended reaction, a mechanical high-pressure generator 16 can be used to increase the pressure to the desired value.

The methane from cylinder 12 is then introduced into a stainless steel high pressure view cell or reactor 18 through a series of valves, generally depicted by the numeral 20. The view cell 20 can contain water, a stir bar, and catalyst or radical initiator as needed for the intended reaction. Once the methane is charged to the view cell 18, valves 20 are closed, and a circulating temperature bath 22 is used to lower and maintain the view cell 18 at a desired level. The temperature is dependent upon the methane pressure within the view cell 18. Once the lower temperature of the view cell 18 is reached, preferably about 0 to 14° C., the mixture contained in the view cell is allowed to react for about 20 to 60 hours to form methane hydrate.

The methane hydrate in the view cell 18 is then illuminated by light source 24. The light source can be a full spectrum high-pressure mercury vapor lamp emitting light in both the ultraviolet and visible spectrum. More specifically, and as described in the '858 patent, the light source 24 can be a high pressure, quartz mercury-vapor lamp. To separate reactions initiated by radiation with UV light from reactions initiated by visible light, the lamp is enveloped by a filter 26 to block UV light. One exemplary filter is a Pyrex® sleeve fitted around the lamp. The sleeve blocks virtually all radiation below approximately 310 nm emanating from the lamp. The preferred wavelength range is at least 400 nm, for a time between one (1) second and eight (8) hours.

After illumination of the methane hydrate, the temperature of the circulating temperature bath 22 is increased, thus decomposing the methane hydrate into methanol, hydrogen, water, unreacted methane, and carbon monoxide.

The above describe process can be modified to include conversion of methane hydrates by light where a radical initiator has been added to the methane hydrate mix.

The process can be further modified to include the photoconversion of methane hydrates with light where a photocatalyst, doped by a suitable metal and an electron transfer agent to produce methanol and hydrogen. Examples of appropriate photocatalysts include oxide salts of tungsten, titanium, or zirconium; suitable metal dopants include copper, lanthanum, platinum, or lithium.

EXAMPLES

Example 1

Methane hydrate is formed by cooling forty (40) mL of water and methane at 1200 PSIG within a high pressure view cell, with the hydrate formed above 0° C. After formation of the hydrate, the temperature of the view cell was reduced to a low temperature of 5° C. below zero. When the low temperature was achieved, a high-pressure mercury vapor lamp was used to illuminate the hydrate through the view cell's window. After the reaction, the cell was warmed to room temperature and the pressure released. The products of reaction were analyzed by an on-line mass spectrometer, which showed the presence of methanol, hydrogen, unreacted methane, and carbon monoxide.

Example 2

Methane hydrate was formed by cooling forty (40) mL of water with a radical initiator (20 µL 30% $H_2O_2$) and methane at 1200 PSIG within a high-pressure view cell. The hydrate was formed above 0° C. After formation of the hydrate, the temperature of the view cell was reduced to 5° C. below zero. When the low temperature was achieved, a high-pressure mercury vapor lamp was used to illuminate the hydrate through the view cell's window. After the reaction, the cell was warmed to room temperature and the pressure released. The products of reaction were analyzed by an on-line mass spectrometer, which showed the presence of methanol, hydrogen, unreacted methane, and carbon monoxide.

Example 3

Methane hydrate was formed by cooling forty (40) mL of water (containing 0.25 grams of tungsten oxide doped with copper and 0.01 grams of the electron transfer reagent methyl viologen) and methane at 150 PSIG within a high-pressure view cell. The hydrate was formed above 0° C. After formation of the hydrate, the temperature of the view cell was reduced to a low temperature of 5° C. below zero. When the low temperature was achieved, a high-pressure mercury vapor lamp was used to illuminate the hydrate through the view cell's window. After the reaction, the cell was warmed to room temperature and the pressure released. The products of reaction were analyzed by an on-line mass spectrometer, which showed the presence of methanol, hydrogen, unreacted methane, and carbon monoxide.

Example 4

Methane Hydrate was formed by cooling forty (40) mL of water (containing 0.25 grams of tungsten oxide dope with copper and 0.01 grams of the electron transfer reagent methyl viologen) and methane at 1200 PSIG within a high-pressure view cell. The hydrate was formed above 0° C. After formation of the hydrate, the temperature of the view cell was reduced to a low temperature of 5° C. below zero. When the low temperature was achieved, a high-pressure mercury vapor lamp was used to illuminate the hydrate through the view cell's window. After the reaction, the cell was warmed to room temperature and the pressure released. The products of reaction were analyzed by an on-line mass spectrometer, which showed the presence of methanol, hydrogen, unreacted methane, and carbon monoxide.

Referring to FIGS. 2, 3, 4 and 5, there are shown representative data plots. The data shown was obtained by warming the reactor 18 in FIG. 1 to dissociate the methane hydrate. A mass spectrometer (MS) was connected to a port on the reactor 18, and the reactor was vented through the port. The MS analyzed the gases from venting until the reactor reached room pressure.

Figure 2:
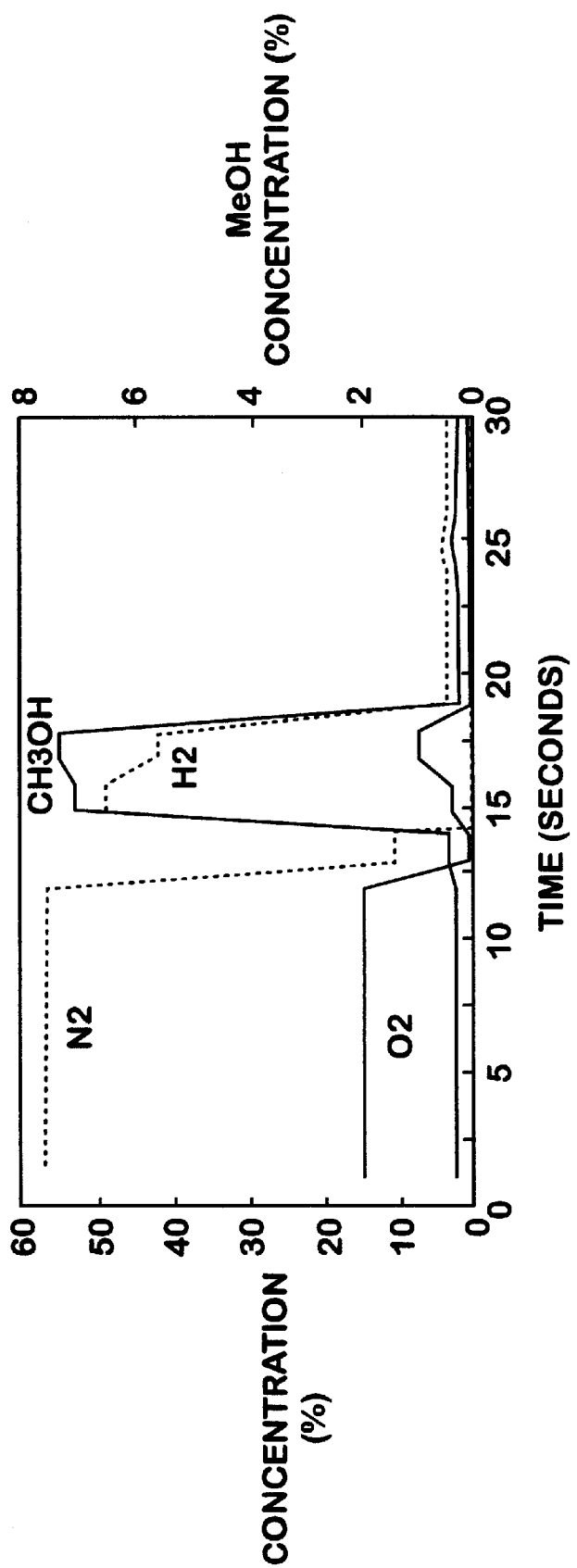
FIGS. 2, 3, 4 and 5 are graphs showing methane hydrate conversion data, in accordance with the present invention.
Figure 3:
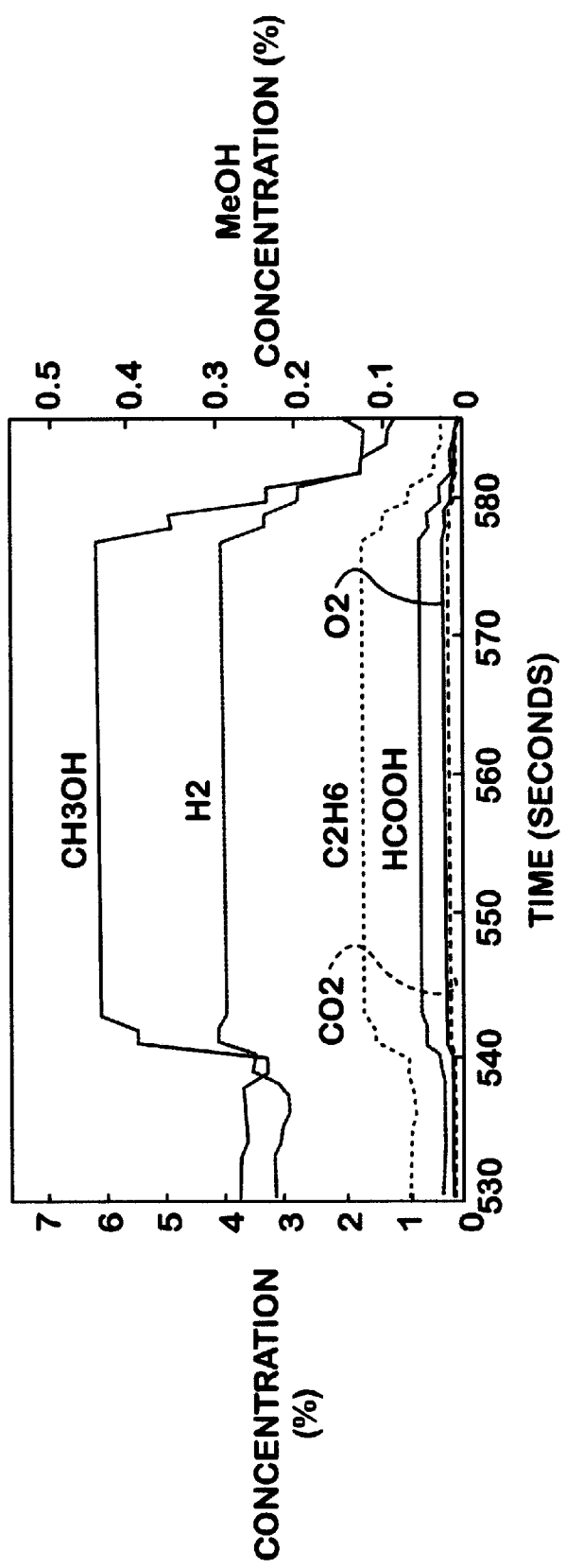

FIGS. 2 and 3 show the conversion of methane hydrate with the photocatalyst. In this example, the sample was illuminated for one (1) hour. FIG. 2 shows the purging of the MS line of room air during the first 12 seconds. After the line is purged, the products of reaction are shown in the plot. FIG. 3 shows the same experiment at a later time in the purge cycle. This data shows more of the products of reaction. That is, the minor products that were not evident in FIG. 2 due to the larger amount of methanol which first masked the smaller peaks.

Figure 4:
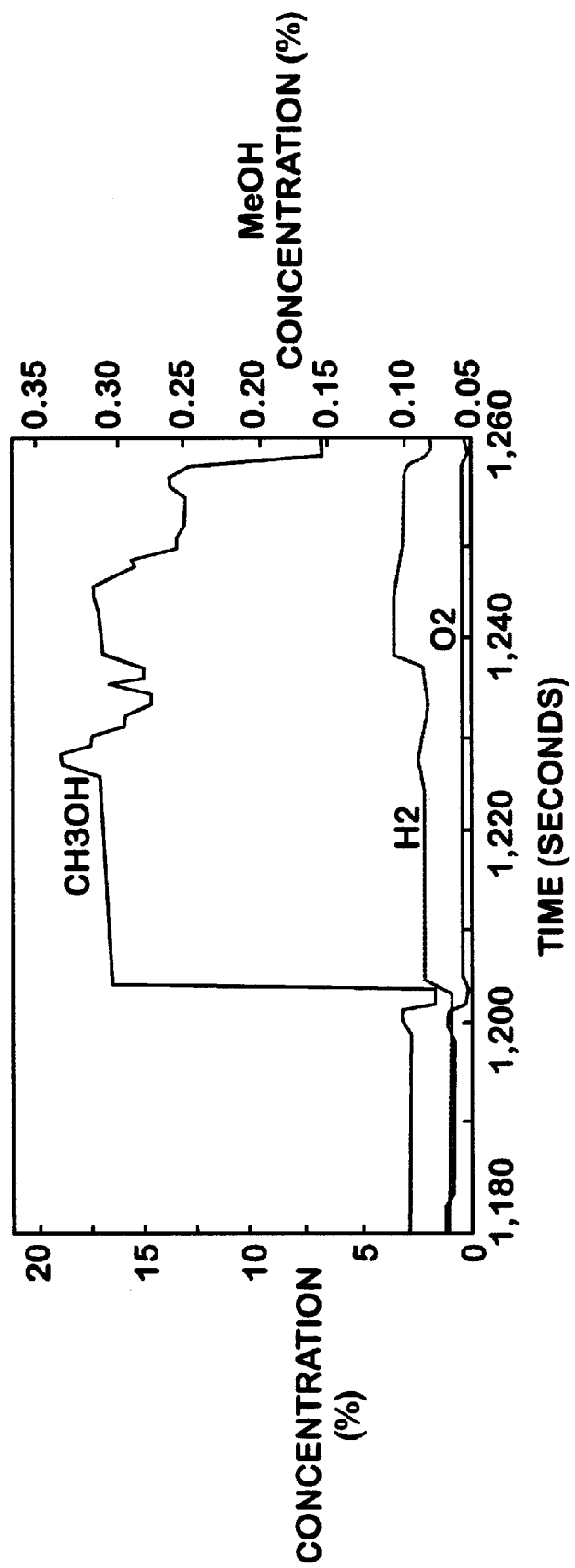

FIG. 4 shows the products of reaction of methane hydrate using a radical initiator. In this experiment the hydrate was illuminated for two (2) hours.

Figure 5:
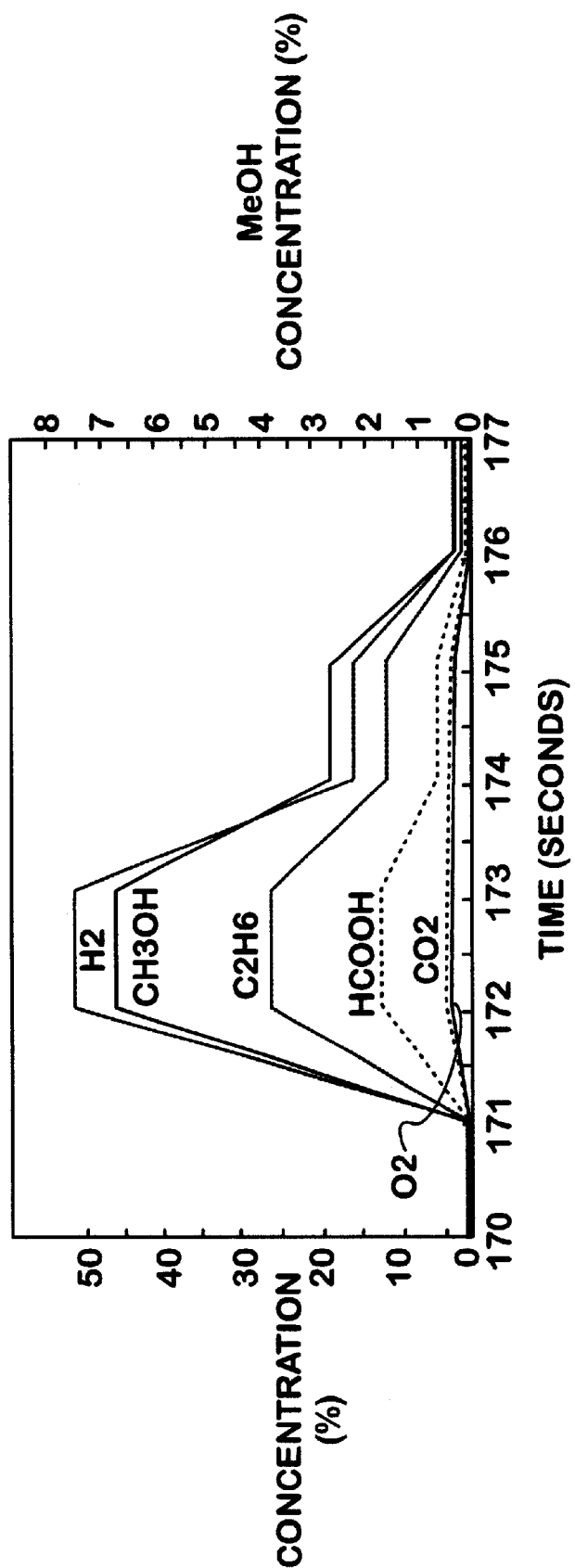

FIG. 5 shows the products of reaction of methane hydrate only. In this experiment the hydrate was illuminated for eight (8) hours. The products of reaction are the same as those observed in FIGS. 2, 3, and 4.

A practical application of the disclosed invention is for the removal of hydrate plugs that occur in wells. When a well is drilled to recover oil and/or natural gas (methane), there exists the possibility that under certain conditions a plug of methane hydrate will form in the well or pipelines. This plug stops the flow through the well or pipeline, resulting in downtime and lost productivity. This problem is most evident when production from the well must be shut down for any period of time. Currently, when a shut down is planned, the well is flooded with methanol to prevent the formation of hydrates. The use of methanol for hydrate prevention is expensive and requires that large quantities of methanol be stored on the production platform. It is envisioned that this invention could be used to dissociate the plug by the use of a fiberoptic light tube inserted into the well or pipeline and placed in front of the plug. The light source would be turned on to begin the reaction. The methane contained within the hydrate plug would be converted to methanol, a liquid, and eventually the plug will no longer be present. An alternative would be to deliver a radical initiator to the surface of the hydrate before turning on the light source. Yet another alternative would be the delivery of a photocatalyst to the surface of the hydrate before turning on the light source.

The foregoing description of a preferred embodiment of the invention has been presented for purposes of illustration and description. It is not intended to be exhaustive or to limit the invention to the precise form disclosed, and obviously many modifications and variations are possible in light of the above teaching. The embodiment was chosen and described to best explain the principles of the invention and its practical application and thereby enable others skilled in the art to best utilize the invention in various embodiments and with various modifications as are suited to the particular use contemplated. It is intended that the scope of the invention be defined by the claims appended hereto.

The embodiment of the invention in which an exclusive property or privilege is claimed is defined as follows:

1. A method for converting methane hydrates to produce methanol comprising:
   a) illuminating a mixture of methane hydrate with a light source,
   b) raising the temperature of the methane hydrate mixture, and
   c) allowing the methane hydrate mixture to convert into methanol.

2. The method of claim 1 wherein the light source has visible wavelength of at least 400 nm.

3. The method of claim 2 wherein the conversion occurs below 0° C.

4. The method of claim 3 wherein a photocatalyst doped by a metal and an electron transfer reagent is added to the methane hydrate mixture.

5. The method of claim 4 wherein the photocatalyst is an oxide salt of tungsten, titanium, or zirconium, and the metal dopant is copper, lanthanum, platinum, or lithium.

6. The method of claim 5 wherein the electron transfer reagent is methyl viologen.

* * * * *